United States Patent
Gardiner (10) Patent No.: US 11,376,341 B2
(45) Date of Patent: Jul. 5, 2022

(54) SANITIZATION AND CLEANING SYSTEM FOR OBJECTS

(71) Applicant: Kart Kleen LLC, Missoula, MT (US)

(72) Inventor: Jason Gardiner, Missoula, MT (US)

(73) Assignee: Kart Kleen LLC, Missoula, MT (US)

( * ) Notice: Subject to any disclaimer, the term of this patent is extended or adjusted under 35 U.S.C. 154(b) by 156 days.

(21) Appl. No.: 16/368,423

(22) Filed: Mar. 28, 2019

(65) Prior Publication Data

US 2020/0306395 A1 Oct. 1, 2020

(51) Int. Cl.
*A61L 2/10* (2006.01)
*A61L 2/26* (2006.01)
*B62B 3/00* (2006.01)

(52) U.S. Cl.
CPC ............... *A61L 2/10* (2013.01); *A61L 2/26* (2013.01); *B62B 3/002* (2013.01); *A61L 2202/11* (2013.01); *A61L 2202/20* (2013.01)

(58) Field of Classification Search
CPC ........................................ B62B 3/002
See application file for complete search history.

(56) References Cited

U.S. PATENT DOCUMENTS

| | | | | |
|---|---|---|---|---|
| 3,179,117 A | * | 4/1965 | Gibson | B60P 3/00 134/107 |
| 3,236,960 A | * | 2/1966 | Larson | H01H 35/00 200/61.41 |
| 3,444,867 A | * | 5/1969 | Thornton | B60S 3/04 134/123 |
| 3,698,029 A | * | 10/1972 | Pulliam | B08B 1/02 15/88.3 |
| 4,279,263 A | * | 7/1981 | Pulliam | B60S 3/044 134/111 |
| 4,992,247 A | * | 2/1991 | Foti | A61L 2/20 422/28 |
| 5,258,162 A | * | 11/1993 | Andersson | B65B 55/10 422/28 |
| 5,622,196 A | * | 4/1997 | Luongo | B08B 3/022 134/131 |

(Continued)

OTHER PUBLICATIONS

ClorDiSys Solutions, Inc., "Chlorine Dioxide Gas Decontamination: Ultraviolet Light Disinfection," retrieved from <<https://www.clordisys.com/>> on Jan. 15, 2020, available as early as Dec. 26, 2019, 1 page.

(Continued)

*Primary Examiner* — Regina M Yoo
(74) *Attorney, Agent, or Firm* — Lee & Hayes, P.C.

(57) ABSTRACT

Systems and techniques for cleaning and sanitizing objects are discussed herein. An object may include an unpowered object such as a shopping cart or a powered object such as a power wheel-chair. A sanitization structure may be connected to a reservoir and may apply a sanitizing agent to the object via one or more nozzles. A drying structure may apply filtered gas such as filtered air to the object via one or more air ducts. An ultraviolet (UV) light structure may apply UV light to the object via one or more UV lamps. A UV curtain structure may include one or more curtains that block the UV light. A bumper rail may guide the object received by the various structures from an entrance side to an exit side of the various structures.

20 Claims, 8 Drawing Sheets

(56) References Cited

U.S. PATENT DOCUMENTS

| | | | | |
|---|---|---|---|---|
| 5,792,435 | A * | 8/1998 | Mueller | A61L 2/24 422/292 |
| 5,879,648 | A * | 3/1999 | Hada | A61L 2/20 422/28 |
| 6,077,480 | A * | 6/2000 | Edwards | A61L 2/208 422/105 |
| 6,090,218 | A * | 7/2000 | Brackmann | A47F 10/04 134/123 |
| 6,120,730 | A * | 9/2000 | Palaniappan | B65B 55/10 422/28 |
| 6,702,985 | B1 * | 3/2004 | Taggart | B67C 7/0073 222/356 |
| 7,300,522 | B2 * | 11/2007 | Feistmanti | B08B 1/02 134/124 |
| 7,346,956 | B2 * | 3/2008 | Andre | B60S 3/002 15/302 |
| 7,516,967 | B2 * | 4/2009 | Schwei | A61L 2/18 134/15 |
| 7,621,285 | B2 * | 11/2009 | Robert | B08B 3/022 134/61 |
| 8,071,021 | B2 * | 12/2011 | Hill | A61L 9/22 422/28 |
| 8,349,272 | B2 * | 1/2013 | Hill | A61L 9/22 422/304 |
| 8,621,824 | B2 * | 1/2014 | Mielnik | B65B 55/02 53/167 |
| 2002/0159915 | A1 * | 10/2002 | Zelina | B65B 55/10 422/3 |
| 2005/0217701 | A1 | 10/2005 | Holbrook | |
| 2005/0276722 | A1 | 12/2005 | Hilton | |
| 2006/0151714 | A1 * | 7/2006 | Thilly | B65B 3/003 250/453.11 |
| 2006/0186358 | A1 | 8/2006 | Couvillion | |
| 2007/0012340 | A1 | 1/2007 | Jones et al. | |
| 2008/0178412 | A1 | 7/2008 | Kiter | |
| 2009/0050174 | A1 | 2/2009 | Gheparde | |
| 2010/0122717 | A1 * | 5/2010 | Yoon | A61L 2/22 134/137 |
| 2011/0068496 | A1 * | 3/2011 | Atkinson | B29C 35/045 264/2.6 |
| 2012/0219387 | A1 * | 8/2012 | Atkinson | B29C 35/045 414/160 |
| 2013/0078327 | A1 * | 3/2013 | Adriansens | B29C 49/68 425/210 |
| 2017/0156376 | A1 * | 6/2017 | Van Appeldoorn | B65B 25/22 |
| 2017/0340760 | A1 | 11/2017 | Starkweather et al. | |

OTHER PUBLICATIONS

Dall, "UV-light cleaning shown to cut superbugs hospital-wide," retrieved from <<http://www.cidrap.umn.edu/news-perspective/2018/06/uv-light-cleaning-shown-cut-superbugs-hospital-wide>> on Jan. 22, 2020, CIDRAP News, University of Minnesota, Jun. 5, 2018, 2 pages.

Duke Health, "UV light can aid hospitals' fight to wipe out drug-resistant superbugs," retrieved from <<https://www.sciencedaily.com/releases/2017/01/170117083836.htm>> on Jan. 22, 2020, ScienceDaily, Jan. 17, 2017, 2 pages.

Nikitovic-Jokic, et al., "Portable Ultraviolet Light Surface-Disinfecting Devices for Prevention of Hospital-Acquired Infections: A Health Technology Assessment," Ontario Health Technology Assessment Series, Health Quality Ontario, vol. 18, No. 1, Feb. 2018, pp. 1-73.

Proximity Systems, "Ultraviolet Disinfection With UV-Clean No-Touch Technology," retrieved from <<https://proximitysystems.com/uvclean/>> on Jan. 15, 2020, available as early as Dec. 26, 2019, 6 pages.

Surfacide, "Meet the Helios System," retrieved from <<http://www.surfacide.com/>> on Jan. 15, 2020, available as early as Dec. 26, 2019, 9 pages.

The Buggy Bath, "Shopping Cart Cleaning System: The Buggy Bath Shopping Cart Sanitizing," retrieved from <<http://www.thebuggybath.com/>> on Jan. 15, 2020, available as early as Dec. 26, 2019, 1 page.

Comfort Mechanical Enterprises, Inc., "Ultra Clean: Ultra Clean Medical Module," retrieved from <<http://cmeincorporated.com/energy-efficiency-products/ultra-clean-2/>> on Jan. 15, 2020, available as early as Dec. 26, 2019, 5 pages.

American Ultraviolet, "Healthcare Solutions: UVC for Healthcare," retrieved from <<https://www.americanultraviolet.com/germicidal-healthcare-solutions/>> on Jan. 15, 2020, available as early as Dec. 26, 2019, 1 page.

Wiseguide, "4 Best UV Light Sanitizers For Chemical Free Cleaning," retrieved from <<https://www.wiseguide.com/tech/4-best-uv-light-sanitizers-because-you-always-wanted-to-clean-like-harry-potter/>> on Jan. 15, 2020, available as early as Dec. 26, 2019, 5 pages.

Atlantic Ultraviolet, "Sani-Ray Germicidal Ultraviolet Fixtures Owner's Manual: Installation, Operation & Maintenance," Oct. 2018, 12 pgs.

Atlantic Ultraviolet, "Sani-Ray Germicidal Ultraviolet Recessed Fixtures," Specifications, Aug. 2018, 12 pgs.

The PCT Search Report and Written Opinion dated Jun. 15, 2020 for PCT Application No. PCT/US2020/025087, 12 pages.

* cited by examiner

SANITIZATION AND CLEANING SYSTEM FOR OBJECTS

BACKGROUND

On a daily basis, people physically contact, without protection, potentially contaminated objects. Objects may include door handles, tables, rails, benches, shopping carts, and the like. In addition, some retail and non-retail environments may assist in contaminating various objects contained within their respective environments. For instance, medical facilities (e.g., hospitals) and food preparation facilities (e.g., grocery stores or restaurants), as a by-product of their operation, may contribute to the contamination of objects. Further, sensitive environments may need to be sanitized by virtue of their relationship to the public. For instance, medical facilities and food preparation environments need to be regularly cleaned and sanitized to preserve public health and to reduce the number of pathogens and illness causing agents that may be exposed to patents and customers. It is also important for these environments, and their associated institutions and businesses, to satisfy present, and potentially future, legal and regulatory standards relating to public health and safety.

BRIEF DESCRIPTION OF THE DRAWINGS

The detailed description is set forth with reference to the accompanying figures. In the figures, the left-most digit(s) of a reference number identify the figure in which the reference number first appears. The use of the same reference numbers in different figures indicates similar or identical items or features.

DETAILED DESCRIPTION

In the context of public health and safety, people in public and private spaces encounter microorganisms on a daily basis. Some of these microorganisms may be harmful to people. A pathogen (i.e., a germ) may be any type of microorganism that may cause or produce a disease or illness. *E. coli* (i.e., a pathogenic bacteria) may cause at least food poisoning that is harmful to humans. In addition, instances of *E. coli* with respect to food products frequently cause recalls of those food products due to potential food contamination. A recall, such as a request from a store, a manufacturer, or a producer to return a contaminated product, may cause costly disruptions in the business. In particular, a physical environment (e.g., a retail store, a grocery store, or a medical facility) may have a steady flow of people physically interacting with objects (e.g., door handles or shopping carts) during their hours of operation and, therefore, may be susceptible to harboring harmful pathogens. For instance, food preparation businesses including restaurants and delis may be vulnerable to harboring *E. coli* due to the nature of their business handling raw and uncooked food. Therefore, to protect the health of safety of customers, it may be necessary to ensure the sanitization of objects that may be in physical contact with consumers, customers, employees, etc. In addition, limiting the exposure of potentially harmful pathogens may benefit businesses by avoiding the consequences of harboring potentially harmful pathogens (e.g., avoiding recalls).

With respect to the sanitization of physical objects, there is a need for techniques, including processes and apparatuses, that facilitate efficient, high-quality, and reliable sanitization of physical objects. In particular, physical objects, which may be interchangeably referred to as "objects" or "items" herein, may be located within a physical environment (e.g., a grocery store). These objects (e.g., shopping carts, hospital beds, wheelchairs, etc.) may be accessible for physical contact by customers and/or employees. Because these objects are physically handled by customers and/or employees during the course of business, and since these objects may be in physical contact with food items (e.g., raw chicken, unclean produce, etc.), human waste (e.g., feces, urine, vomit, etc.) or other bodily fluids (e.g., saliva, blood, etc.), etc., there is a need to sanitize the objects regularly to guard against potentially harmful pathogens that attach to the objects. For instance, a shopping cart may be physically interacted with by multiple customers during the course of a single day. If the shopping cart were to be harboring a harmful pathogen, each of the multiple customers that handled the shopping may be unwittingly exposed to the harmful pathogen.

Traditional techniques to clean shopping carts for use in a grocery store may include pressure washing or using a towel or scrub brush to wipe down the shopping cart. However, these techniques often neglect eliminating sanitation threats at a microbial level. Further, these techniques may result in wear and tear of an object because they require either physically dislodging contaminants under high pressure (e.g., a pressure of 750 to 30,000 pounds per square inch (PSI)) or physically touching the object.

In addition, there is a need for efficient, high-quality, and reliable results sanitizing multiple objects at a single time or consecutively. In a physical environment, (e.g., a grocery store), there may be additional challenges with implementing sanitization techniques for objects (e.g., shopping carts). For instance, a grocery store may have a designated area for cleaning various equipment. This designated area may be a confined and/or limited in area (e.g., limited as to a quantity of square feet). Therefore, there is a need to develop at least a system, and associated processes, that can operate in an area having a limited amount of space. In light of area related limitations, traditional techniques have included placing a shopping cart in a container, closing a door or bringing down a lid over the container, and starting a cleaning cycle similar to a dish washing machine type technique. However, these techniques may be time-consuming and do not allow for multiple objects (e.g., stacked shopping carts) to be run through the cleaning process efficiently. In addition, these traditional techniques do not allow for multiple and/or different sanitization techniques to be applied to a single object. As described herein, the systems and processes described herein describe the application of a sanitizing agent (e.g., a chemical solution) and ultraviolet (UV) light to an object. Existing systems are unable to accommodate multiple disinfecting techniques. Other existing techniques may include wiping the object off using a cleaning tool (e.g., a towel or a scrubbing brush) or pressure washing the object. However, these techniques may be time consuming and may be inefficient for cleaning multiple objects, either at a single time or consecutively. Further, these techniques may not reliably produce a consistent sanitization quality as the cleanliness of the cleaning object and/or the manual effort used to sanitize the object may vary. In addition, traditional techniques may result in wear and tear on the object as they require physical interaction with the object.

The systems and techniques described herein address the above challenges with respect to cleaning and sanitizing objects. For instance, the systems and techniques herein describe an efficient and repeatable apparatus and process to sanitize an object (or multiple objects). In addition, the systems and techniques herein describe a system that may be used to sanitize multiple objects efficiently and in a timely manner. Further, the systems and techniques herein also include sanitizing objects via an automated or a partially-automated process. These systems and techniques describe a primarily touchless process to sanitize an object in order to reduce wear and tear and/or damage to the object that could potentially occur as a result of the sanitization process. The techniques as described herein are suitable for a number of physical environments including at least grocery stores (or other physical stores where shopping carts are used), locations where raw or uncooked food products are handled, processed, and/or prepared (e.g., restaurants, food processing locations, etc.), and medical facilities (e.g., hospitals, medical clinics, etc.).

The techniques described herein are directed to a sanitization system. In some embodiments, the sanitization system may include a sanitization structure, a drying structure, an ultraviolet (UV) light structure, and/or a UV curtain structure. The various structures may be axially aligned such that an object (e.g., a shopping cart, a hospital bed, a table used to process/prepare food products, etc.) may be received by a first structure (e.g., the sanitization structure or the UV light structure) at an entrance side (i.e., a first side). For instance, the first structure may be an arch or an arch frame (or any other shape, such as rectangular, circular, etc.) with a space with a width (e.g., a span) underneath a horizontal beam or curved arch. The first structure may receive the shopping cart in this space. The shopping cart may then exit the sanitization system at an exit side (i.e., a second side) of a second structure (e.g., the drying structure, the UV light structure, or the UV curtain structure). The sanitization structure, the drying structure, the UV light structure, and/or the UV curtain structure may be permanently or removably fastened/coupled to the ground and/or a surface (e.g., a platform and/or a ramp). However, the structures described herein may also be mobile in nature, and may be moved in any direction using wheels, rollers, a slider, etc. In some instances, an "entrance" or "enter" sign may be coupled on an entrance side of one or more of the sanitization structure, the drying structure, the UV light structure, or the UV curtain structure. In addition, an "exit" sign may be coupled to an exit side of one or more of the sanitization structure, the drying structure, the UV light structure, or the UV curtain structure. That way, an individual that is facilitating the sanitization of the object(s) may determine an entrance point of the sanitization system.

In various embodiments, the shopping cart may move or may be moved a distance spanning from the entrance side (e.g., an entrance side of the sanitization structure) to the exit side (e.g., the exit side of the UV curtain structure) via manual and automated means. With respect to manual means, one or more objects (e.g., shopping carts) may be pushed or pulled by hand to move the distance spanning from the entrance side to the exit side. One or more objects may also be pulled or pushed using a rope (e.g., a control rope coupled to the object), a chain link, a lead, a braided hose, or other suitable flexible and/or rigid devices. In various embodiments, the object may be received at the entrance side and travel the distance to the exit side using automated means. For instance, the shopping cart may be placed on a conveyer belt, a moving sidewalk (e.g., an auto walk), an escalator (e.g., an inclined moving sidewalk), a shuttle that is coupled to a track and/or grooves, an object conveyer that couples to the object, or other suitable automated devices that move the object(s) from a first side of the sanitization system (e.g., the entrance) to a second side of the sanitization system (e.g., the exit).

In various embodiments, the sanitization structure may be coupled to a reservoir that contains a sanitizing agent. The sanitization structure may include a sanitizing agent tube that connects one or more nozzles to the reservoir, such that the sanitizing agent is in fluid communication contained in the reservoir is in fluid communication with the nozzle(s). The reservoir cause filtered water to be mixed with the sanitizing agent such that the filtered water/sanitizing agent combination is dispersed by the one or more nozzles. The one or more nozzles may be configured to apply the sanitizing agent to the shopping cart. For instance, the nozzles may mist the shopping cart with a layer of the sanitizing agent. The sanitizing agent may be any anti-microbial sanitation solution or any anti-bacterial chemical that can disable, remove, or destroy potentially harmful pathogens. In some instances, the one or more nozzles may apply the sanitizing agent in continuous manner or at an interval. The sanitizing agent may be configured to be evaporable.

In various embodiments, the drying structure may include one or more fans, or one or more directional blowers, that are configured to draw in air from the atmosphere and/or a gas. An air purifier 130 may then receive the air, filter out particulates (e.g., dust), to produce filtered air. The drying structure may also include one or more air ducts to apply the filtered air to the shopping cart. The one or more fans, the air purifier 130, and the one or more air ducts may be coupled and/or connected via purification tunnel. The purification tunnel may be a tube and/or pipe that facilitates the movement of a gas (e.g., the filtered air). The filtered air may be applied via the one or more air ducts to remove moisture present on the shopping cart. For instance, the filtered air may dry the sanitizing agent such that little to no sanitizing agent remains on the object(s). In other embodiments, an object may be previously wet (e.g., a shopping cart being wet as a result of rainy or snowy weather). The drying structure may apply the filtered air to the object to dry the object. In some instances, as stated above, the one or more nozzles may apply the sanitizing agent in continuous manner or at an interval. However, in some instances, an object may not have the sanitizing agent applied via the sanitization structure, or the sanitization structure may not be present in the sanitization system, and the object may be moved towards the drying structure to be dried. In some instances, the air purifier 130 may be an air scrubber that removes gases or particles from the air. For instance, an air scrubber may be used to remove carbon dioxide from the air.

In various embodiments, the UV light structure may include one or more UV lamps that are configured to apply UV light to the shopping cart. The one or more UV lamps may be configured to emit light at a wavelength outside of the visible spectrum that disables, breaks down, and/or destroys pathogenic organisms (e.g., bacteria). The one or more lamps may be housed in one or more UV lamp housings 136 to provide directional application of the UV light to the shopping cart.

In various embodiments, the UV curtain structure may include one or more UV curtains. The one or more UV curtains may be configured to block an entirety or a portion of the UV light emitted from the one or more UV lamps. In some instances, the sanitization structure, the drying structure, the UV light structure, and/or the UV curtain structure may be encapsulated or surrounded by a tunnel. The tunnel may be co-axially aligned with at least one of the sanitization structure, the drying structure, the UV light structure, or the UV curtain structure. The tunnel may have an entrance side and an exit side. In some instances, the tunnel may be made from a polyethylene material that reduces visibility of processes performed by the sanitization structure, the drying structure, the UV light structure, and/or the UV curtain structure. That is, customers may only see the tunnel, and may not have visibility of the techniques used by the structures to clean and sanitize objects.

In various embodiments, bumper rails may extend from the sanitization structure (or any other of the structures) to at least one of the drying structure, the UV light structure, or UV curtain structure. For instance, the sanitization structure may be an arch with an inner side located adjacent to the space within or beneath the arch. The UV curtain structure may have a similar arch structure. A first bumper rail may extend from a first side, of the inner side of the sanitization structure, to a first side, of the inner side of the UV curtain structure. A second bumper rail may extend from a second side, of the inner side of the sanitization structure, to a second side, of the inner side of the UV curtain structure. The second bumper rail may be parallel or near-parallel to the first bumper rail. The bumper rail may be configured to cause the object to only be able to exit the sanitization system at an exit side of the sanitization system. A drain (e.g., a grated floor) may span at least a portion of the width between the first bumper rail and the second bumper rail. The drain may collect any fluid (e.g., sanitizing agent) that is applied to the object(s) and that drips from the object(s), or any fluid that is not applied directly to the object(s) and collects on a surface underneath or around the object(s). In some instances, the drain may include a funnel underneath the grated floor for collection of unused sanitizing agent (or sanitizing agent that is applied to the object(s) and that drips/falls off).

In various embodiments, a sensor (e.g., a motion sensor) may be located on or coupled to at least one of the sanitization structure, the drying structure, the UV light structure, and/or the UV curtain structure. The sensor may be configured to detect the object when the object is within a threshold distance (e.g., 1 foot, 2 feet, 5 feet, 10 feet, etc.) from one of the structures. In response to detecting the object, at least one of the sanitization structure, the drying structure, the UV light structure, and/or the UV curtain structure may activate (e.g., commence application of the sanitizing agent, gas current, and/or UV light). For instance, in response to detecting the object(s) (e.g., a single shopping cart, multiple stacked shopping carts, etc.), the sanitization structure may activate to apply the sanitizing agent to the object. The sanitization structure, the drying structure, the UV light structure, and/or the UV curtain structure may also de-activate or cease operation if the motion sensor no longer detects the object(s). For instance, provided that the sensor is positioned on the sanitization structure directed towards the entrance of the sanitization system, the sensor may detect the object(s) when they come in proximity to the sanitization structure. Upon detection, the nozzle(s) of the sanitization structure may apply or disperse the sanitizing agent. Once the object(s) move underneath or through the sanitization structure, the sensor may no longer detect the object(s). As a result, the nozzle(s) may cease applying/dispersing the sanitizing agent, since there are no objects that are currently underneath the sanitization structure.

In various embodiments, a timer and a display may be coupled to at least one the sanitization structure, the drying structure, the UV light structure, the UV curtain structure, and/or an interior or exterior of the tunnel. In response to detecting the object(s), a timer may count down or count up to a predetermined sanitization time. For instance, when the object(s) are detected, a time counting down from six seconds (i.e., the predetermined sanitization time) may begin. In some instances, upon the predetermined sanitization time being reached (e.g., the object(s) have been within the sanitization system for at least six seconds), an audible cue may be emitted from a speaker and/or another audio device to indicate the predetermined sanitization time has been reached. Alternatively, a visual cue may be displayed via the display that indicates that the predetermined sanitization time has been reached. The predetermined sanitization time may be a time that represents a standardized amount of time that an object should spend in the sanitization system in order to meet a threshold sanitization level. The threshold sanitization level may be a predetermined sanitization level associated with removing at least a majority of (or a different level, such as 90%, 95%, 99%, etc.) potentially harmful pathogens. In some instances, a timer may be coupled to the sanitization structure, the drying structure, the UV light structure, the UV curtain structure, and/or the tunnel. An operator of the sanitization system may utilize the timer to determine a length of time the object(s) spend in the sanitization system.

In various embodiments, a power source (e.g., a source of electric power) may be a component that supplies power to at least one of the sanitization structure, the drying structure, the UV light structure, and/or the UV curtain structure. In some instances, a separate power source may supply electric power to each structure, a single power source may supply electric power to each of the structures, or different power sources may supply electric power to multiple, but not all of, the structure.

In various embodiments, one or more of the sanitization structure, the drying structure, the UV light structure, or the UV curtain structure may be coupled to an emergency shut-off. An emergency shut-off may be a manual button or switch (or a selectable element actuable via the display) that turns-off, de-activates, and/or shuts down one or more of the sanitization structures, such as the sanitization structure, the drying structure, and/or the UV light structure. For instance, the emergency shut-off may be a lever that, when manually switched by an operator of the sanitization system, immediately ceases application of the sanitizing agent by the sanitization structure.

In various embodiments, the sanitizing agent may be applied to the object via one or more nozzles coupled to the sanitizing structure at a first time, the gas current may be applied to the object via one or more air ducts coupled to the drying structure at a second time that is subsequent to the first time, and UV light may be applied via one or more UV lamps coupled to a UV light structure at a third time that is subsequent to the second time. However, the different structures of the sanitization system described herein may be arranged in any order or configuration. For instance, the sanitization structure may apply the sanitizing agent first, the UV light structure may apply the UV light second, and then the drying structure may apply the purified air last. In further embodiments, provided that the structures are moveable, the structures may be moved between different configurations or arrangements.

Figure 1:
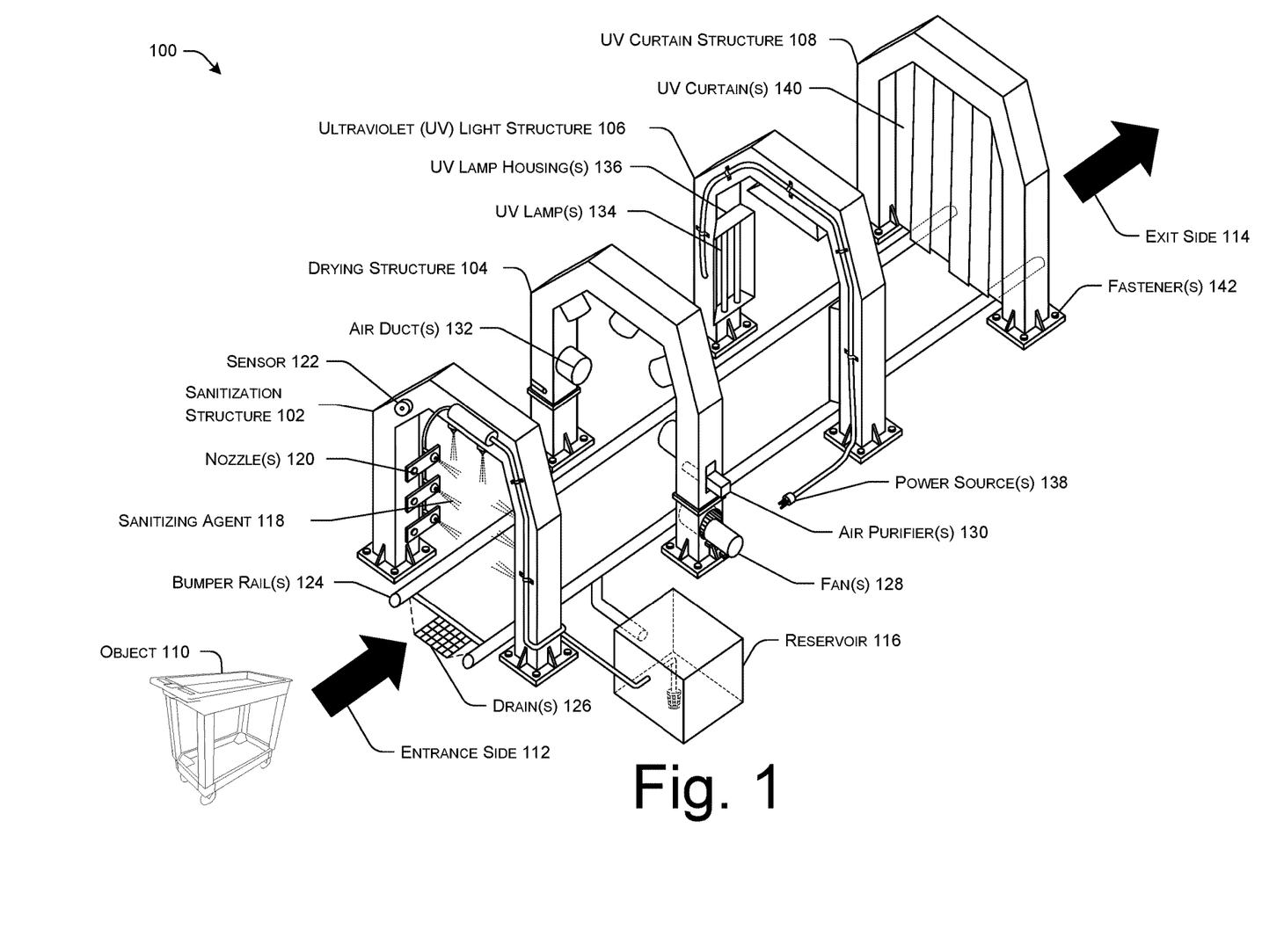
FIG. 1 is a pictorial diagram of an illustrative system that includes multiple structures to facilitate sanitization of one or more objects.

FIG. 1 is a pictorial diagram of an illustrative apparatus that includes multiple structures to facilitate sanitization of one or more objects. The pictorial diagram 100 includes at least a sanitization structure 102, a drying structure 104, a UV light structure 106, and a UV curtain structure 108. The sanitization structure 102, the drying structure 104, the UV light structure 106, and/or the UV curtain structure 108 may be axially aligned. In some instances, at least one of the sanitization structure 102, the drying structure 104, the UV light structure 106, and/or the UV curtain structure 108 may not be axially aligned with the various other structures. As shown, each of the sanitization structure 102, the drying structure 104, the UV light structure 106, and/or the UV curtain structure 108 may be configured to receive an object 110 at an entrance side 112. As shown, the object 110 may be received by the sanitization structure 102 at the entrance side 112 and exit the UV curtain structure 108 at an exit side 114. In some instances, each of the sanitization structure 102, the drying structure 104, the UV light structure 106, and/or the UV curtain structure 108 may individually have an exit and an entrance. For instance, the sanitization structure may have an entrance on the entrance side 112 (e.g., where the object 110 enters the sanitization structure 102) and an exit on the opposite side or exit side 114 (e.g., where the object 110 exits the sanitization structure 102).

The object 110 may be any unpowered or a powered object 110. An unpowered object 110 may include objects 110 that require external assistance to move, unless the unpowered object(s) 110 are moved via an automated or partially-automated mechanism, such as a conveyor. For instance, an unpowered object 110 may include a shopping cart, a push cart, a pallet, a table (e.g., for handling, processing, or preparing facility, such as a hospital bed). In some instances, the object 110 may be a plurality of objects 110. For instance, the object 110 may be a plurality of stacked shopping carts where a shopping cart of the plurality of shopping carts is configured to physically couple to another shopping cart of the plurality of shopping carts. If the object 110 requires external assistance to move, the object 110 may be moved using a suitable manual device (e.g., a rope operated by a person) or automated device (e.g., a conveyor) to travel a distance between the entrance side 112 and the exit side 114. An object 110 may also be a powered object 110 that is able to travel the distance between the entrance side 112 and the exit side 114 with assistance. For instance, the powered object 110 may include a self-driving cart or a motor vehicle that includes at least a motor or battery and a means for navigation (e.g., sensors).

As shown, the object 110 illustrated in FIG. 1 appears to depict a push cart that may require external assistance to travel the distance between an entrance side 112 and an exit side 114 of the sanitization system.

In some embodiments, the object(s) 110 may be of any size and the sanitization system 100 may also be of any size. That is, the sanitization system 100 may be of any height, length, and/or width. For instance, the sanitization system 100, as well as the various structures associated therewith (e.g., the sanitizing structure 102, the drying structure 104, the UV light structure 106, and/or the UV curtain structure 108), may be of suitable size in order to allow the object(s) 110 to pass through, by, or underneath the structures. For instance, and as described herein, the sanitization system 100 may clean/sanitize smaller objects 110, such as shopping carts, hospital beds, wheelchairs, food preparation carts/tables, etc. However, the sanitization system 100 may be of a suitable size to clean/sanitize larger objects 110, such as trucks that transport livestock (e.g., livestock trailers that transport cows, horses, etc.) or food products (e.g., grain, hay, produce, etc.), food conveyor belt trucks, grain truck beds, food trailers, farming equipment (e.g., tractors, plows, irrigation equipment, etc.), and so on. For the purposes of this discussion, the sanitization system 100 may be built to any size and/or may be adjustable to any size, thereby allowing the sanitization system 100 to clean and sanitize objects 100 of any size.

As shown, the sanitization structure 102 may be coupled to a reservoir 116. The reservoir 116 may include a container that is configured to hold liquid such as water and/or a cleansing agent. In some instances, the reservoir 116 may include a filter that is configured to filter water or the cleansing agent (e.g., remove particles and/or contaminants from water/cleansing agent). The cleansing agent may be composed of anti-pathogen compounds such as triclosan, triclocarban, benzalkonium chloride, benzethonium chloride, chloroxylenol, and/or other suitable compounds that at least assist in destroying, disabling, and/or removing pathogens. The cleansing agent may be a chemical that destroys, removes, and/or disables pathogens, bacteria, food items, dirt, etc. In some instances, a liquid and a cleansing agent may be combined to form a sanitizing agent 118. Alternatively, the cleansing agent itself may be the sanitizing agent 118. The sanitizing agent 118 may be a liquid sanitizer that is configured as an anti-microbial sanitization solution. As shown, the reservoir 116 is coupled to one or more nozzles 120 via one or more tubes or pipes that transport the sanitizing agent 118 from the reservoir 116 to the nozzle(s) 120. The one or more nozzles 120 may be configured to apply or disperse a mist or spray of the sanitizing agent 118 onto the object(s) 110. In some instances, the one or more nozzles 120 may include rotating, or movable, misting heads to ensure full coverage of the object(s) 110 with the sanitizing agent 118. The one or more nozzles 120 may also apply a liquid (e.g. water) to the object(s) 110. In some instances, the sanitizing agent 118 may be selected based on a type of pathogen, a group of pathogens, food products, bodily fluids, bacteria, dirt, etc. that may be present on the object(s) 110.

As shown, the sanitization structure 102 may include one or more sensors 122. The sensor(s) 122 may include an active or passive infrared sensor, a microwave sensor, an area reflective sensor, an ultrasonic sensor, a photo optic motion sensor. A, or any other types of sensors that are configured to detect the object(s) 110. The sensor(s) 122 may be any sensor that is configured to detect the object(s) 110. In some instances, the object(s) 110 may be configured to contain a radio transmitter that may send a coded and/or encoded signal (e.g., radio wave) that is received by a receiver on the sensor(s) 122. The sensor(s) 122 may detect the object(s) 110 based on receiving a signal emitted from the object(s) 110. In response to the sensor(s) 122 detecting the object(s) 110, the sanitization structure 102 may activate causing the one or more nozzles 120 to apply the sanitizing agent 118 to the object(s) 110.

As shown, a set of bumper rails 124 may extend from the sanitization structure 102 to the UV curtain structure 108. In some instances, the bumper rail(s) 124 may extend to the drying structure 104 or the UV light structure 106. As shown, a first bumper rail 124 appears to be located on an inside side (e.g., a first side) of the sanitization structure 102 and extends to an inside side (e.g., a first side of UV curtain structure 108). As shown, a second bumper rail 124 appears to be located on an inside side opposite the first side (e.g., a second side) of the sanitization structure 102 and extends to an inside side opposite the first side (e.g., a second side of UV curtain structure 108). As shown, the first bumper rail 124 and the second bumper rail 124 appear to be parallel or near-parallel. In other instances, the first the first bumper rail 124 and the second bumper 124 may not be parallel or near-parallel. For instance, the bumper rail(s) 124 may be a curved or wave shape. The bumper rail(s) 124 may be configured to serve as a guide for the object(s) 110 to follow through the sanitization system. The bumper rail(s) 124 may be composed of at least one of wood, metal, plastic, or other suitable rigid materials.

As shown, one or more drains 126 may span at least a portion of the width between the first bumper rail 124 and the second bumper rail 124. The drain(s) 126 may include a grated floor that spans a distance between the sanitization structure 102 and at least one of the drying structure 104, the UV light structure 106, or the UV curtain structure 108, although the drain(s) 126 may be positioned at any location within the sanitization system 100. In some instances, the drain(s) 126 may be located before a first arch (e.g., the sanitization structure 102 and at least one of the drying structure 104, the UV light structure 106, or the UV curtain structure 108) on the entrance side 112 and/or located after a second arch (e.g., the sanitization structure 102 and at least one of the drying structure 104, the UV light structure 106, or the UV curtain structure 108) on the exit side 114. In some instances, the drain(s) 126 may be located between any grouping of structures, the grouping of structures comprising at least two of the sanitization structure 102 and at least one of the drying structure 104, the UV light structure 106, and the UV curtain structure 108. The drain(s) 126 may be configured to capture liquid and/or the sanitizing agent 118 that has not been applied to the object 110 or has been applied, but run-off, the object 110. In some instances, the drain(s) 126 may include a funnel underneath a grated floor to capture at least unused or run-off of the sanitizing agent 118 that was applied to the object 110.

As shown, the drying structure 104 may include one or more fans 128, one or more air purifiers 130, and one or more air ducts 132. The one or more fans 128 may receive air from the atmosphere (e.g., the area within or surrounding the sanitization system 100). In some instances, the one or more fans 128 may be directional blowers. The one or more fans 128 may be configured move a gas (e.g., air) with an increase in pressure. For instance, a gas may have a first pressure before being drawn in by the one or more fans 128. The one or more fans 128 may cause a movement of the gas at a second pressure, wherein the second pressure is greater than the first pressure. The one or more fans 128 may be coupled to the one or more air purifiers 130. The one or more air purifiers 130, which may be one or more air scrubbers, may receive a gas from the one or more fans 128. The one or more air purifiers 130 may be configured at least to filter the gas to remove contaminants (e.g., dust). In some instances, the one or more air purifiers 130, may transform the gas into a purified gas. For instance, an unfiltered gas may be filtered to remove or to disable pathogens thereby creating a purified (e.g., filtered) gas. The one or more air ducts 132 may receive the purified gas (e.g., a gas current) and apply the gas current to the object(s) 110. At least one air duct 132 of the one or more air ducts 132 may have an air duct opening that is adjustable. For instance, the air duct opening for an air duct 132 may be reduced in size (e.g., reduced in diameter) to apply the gas current to the object 110 at a greater velocity/rate. The one or more air ducts 132 may apply a gas current to dry the object(s) 110 (e.g., to dry any sanitizing agent 118 remaining on the object(s) 110). In some instances, the one or more fans 128, the one or more air purifiers 130, and one or more air ducts 132 may be coupled via a pipe, tunnel, and/or tube that facilitates the movement of gas.

As shown, the UV light structure 106 may include one or more UV lamps 134, one or more UV lamp housings 136, and a power source 138. The one or more UV lamps 134 may apply UV light to the object(s) 110. The one or more UV lamps 134 may be one or more germicidal UV lamps that are configured to emit a light at a wavelength outside of the visible light spectrum to deactivate the deoxyribonucleic acid (DNA) of various pathogens (e.g., bacteria). As shown, the one or more UV lamps 134 may be at least partially contained within the one or more UV lamp housings 136. The one or more UV lamp housings 136 may provide a direction for the one or more UV lamps 134 to emit UV light, thereby assisting in the application of UV light to the object(s) 110. The one or more UV lamp housings 136 may also prevent at least a portion of the UV light emitted from the one or more UV lamps 134 from being emitted in a direction away from the object(s) 110.

As shown, a power source 138 may be coupled to the one or more UV lamps 134 and/or the UV light structure 106 to provide electrical power. As described herein, the power source 138 may be a single power source 138 or multiple power sources 138, and the power source(s) 138 may supply electric power to a single structure, some but not all of the structures, or all of the structures of the sanitization system 100. The power source 138 may have an electrical power setting. For instance, the power source 138 may be at least one of 240 volt (240 v) single phase, 240 v two phase, 240 v three phase, 110-volt single phase, or other suitable voltage and phase settings. In other instances, a second power source 138 may be coupled to the sanitization structure 102 and a third power source 138 may be coupled to the drying structure 104. In some instances, the power source 138 may be coupled to the sanitization structure 102, the drying structure 104, and the UV light structure 106. By way of example, a first power source 138 with a first voltage and/or phase setting may be coupled to at least one of the sanitization structure 102, drying structure 104, or the UV light structure 106, and a second power source 138 with a second voltage and/or phase setting may be coupled at least one of the sanitization structure 102, drying structure 104, or the UV light structure 106. The first voltage and/or phase setting may be different than the second voltage and/or phase setting. The power source 138 may be configured to receive electric power from an electrical producing device or system including receive electrical power via chemical energy, mechanical energy, solar energy, wind energy, geothermal energy, hydrogen energy, hydroelectric energy, and/or biomass energy.

As shown, the UV curtain structure 108 may include, or be coupled to, one or more UV curtains 140. The one or more UV curtains 140 may be a material, such as amber-tinted poly vinyl chloride or other suitable materials, to block at least a portion of the UV light emitted from the one or more UV lamps 134. In some instances, the one or more UV curtains 140 may be configured such that the object 110 may pass through. As shown the UV curtain structure 108 may be fastened or secured to the ground (e.g., concrete) or a surface (e.g., a ramp or platform) via one or more fasteners 142. The one or more fasteners 142 may be based on a material of the ground or surface (e.g., concrete or wood). The one or more fasteners 142 may include screws, anchors, nails, spikes, concrete/cement, adhesive, or other suitable fasteners to permanently or removably fix the UV curtain structure 108 to the ground or to a surface. In addition, the sanitization structure 102, drying structure 104, and the UV light structure 106 may be fixed to the ground or to a surface via one or more fasteners 142 similar to the fasteners 142 coupled to the UV curtain structure 108.

By way of example, a plurality of shopping carts (e.g., the object 110) may be coupled together forming a stack of shopping carts. The plurality of shopping carts may be placed on a moving sidewalk (i.e., automated transported) or pulled via a rope lead (i.e., manually transported) through a sanitization system. The plurality of carts may travel along a path defined by a first and second bumper rail (e.g., one or more bumper rails 124). The plurality of shopping carts may enter a sanitization arch (e.g., the sanitization structure 102) at a first side (e.g., an entrance side 112) of the sanitization arch. A photo optic sensor (e.g., a sensor 122) may detect the plurality of shopping carts. In response to detecting the plurality of shopping carts, the sanitization arch may activate. For instance, a pressurized system may be configured to open a valve allowing the liquid sanitizer (e.g., a sanitizing agent 118 and filtered water) to travel from a reservoir 116 to a plurality of nozzles 120 coupled to the sanitization arch. The liquid sanitizer may be misted or otherwise dispensed via the plurality of nozzles 120 to form a sanitizing layer on the plurality of shopping carts. A drain 126 may be configured to collect run-off of the liquid sanitizer.

Figure 2:
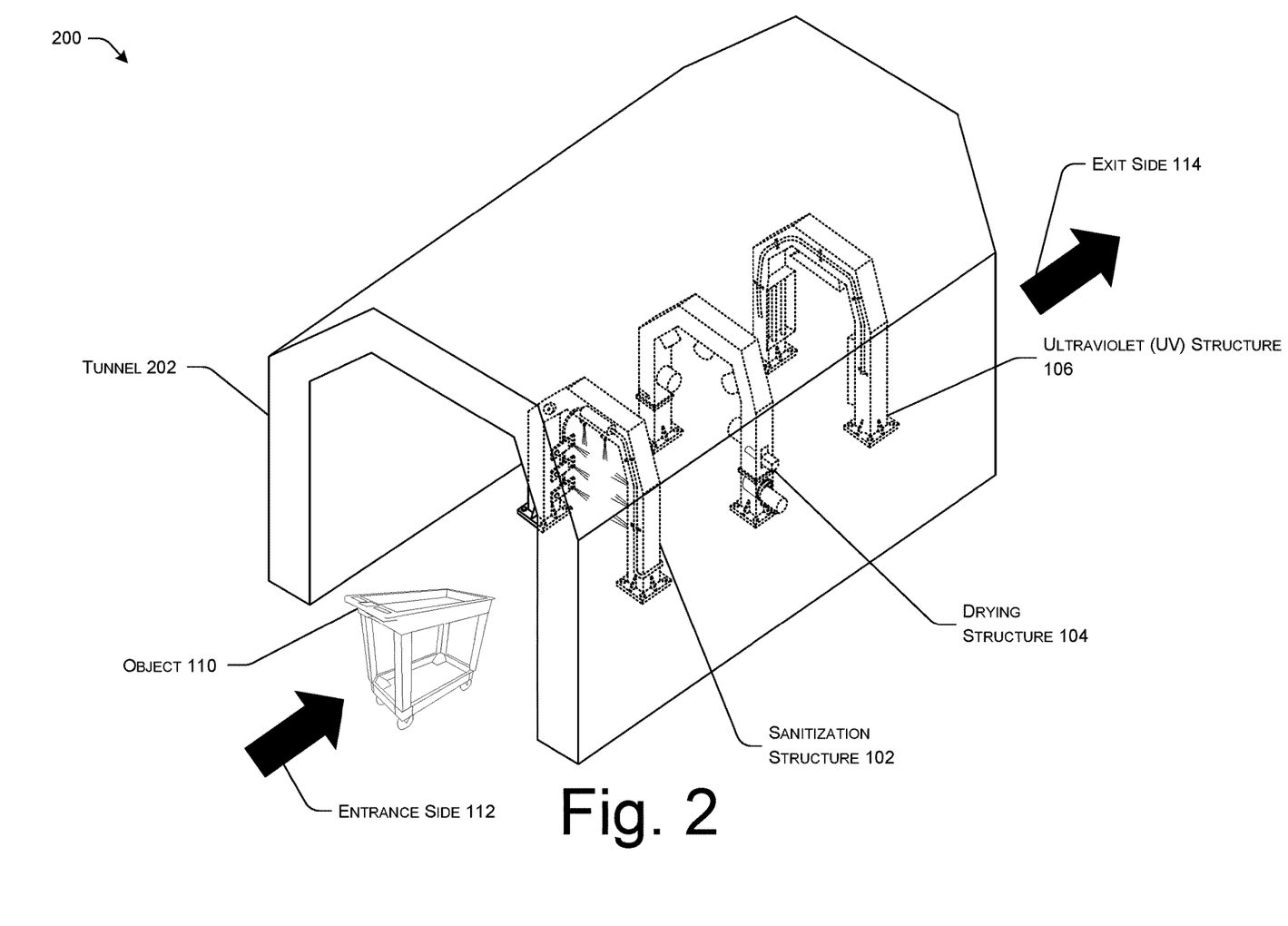
FIG. 2 is a pictorial diagram of an illustrative system that includes a tunnel that at least partially encloses multiple structures that facilitate sanitization of one or more objects.

The plurality of shopping carts may then travel via automated or manual means to a drying arch (e.g., the drying structure 104). A plurality of fans (e.g., one or more fans 128) may draw air from the atmosphere and increase the pressure of the air on a dispensing side of the plurality of fans 128. The drawn air may pass through an air scrubber (e.g., one or more air purifiers 130) to convert unpurified air to purified air by removing contaminants such as dirt and bacteria. The purified air may be applied to the plurality of shopping carts as they pass underneath the arch to dry off any excess liquid sanitizer. The plurality of shopping carts may then travel to a UV light arch (e.g., a UV light structure 106). Germicidal UV light may be applied to the plurality of shopping carts that may disable or destroy one or more pathogens. A UV curtain arch (e.g., the UV curtain structure 108) may block at a least a portion of the UV light to protect passersby. The plurality of shopping carts may exit the UV curtain arch at an exit side of the UV curtain arch (e.g., the exit side 114). The photo optic sensor 122 may detect that there are no remaining shopping carts present in the sanitization system and cause the sanitization arch, the drying arch, and the UV light arch to cease operation and/or to shut down. The entire sanitization system may be encapsulated or encompassed by a tunnel 202 that is composed of a rigid material that can block or resist at least the liquid sanitizer, the purified air, and the UV light. As a result of applying a sanitizing agent 118, purified air, and/or UV light to the shopping carts, which will disable, destroy, and/or remove substances (e.g., bacteria, pathogens, body fluids, human waste, dirt, food products, etc.) residing on the shopping carts, the shopping cars will be cleaned and sanitized for subsequent use. The sanitization system described herein will reduce, and possibly eliminate, the likelihood that individuals (e.g., employees, customers, etc.) will be exposed to potentially harmful substances.

FIG. 2 is a pictorial diagram 200 of an illustrative apparatus that includes a tunnel 202 that at least partially encloses multiple structures. As shown, the tunnel 202 appears to encapsulate or enclose at least the sanitization structure 102, the drying structure 104, and the UV light structure 106. The tunnel 202 may also encapsulated or enclose the UV curtain structure 108. As shown, the object(s) 110 appear to be depicted entering the tunnel on the entrance side 112. The tunnel 202 may be configured to have a tunnel entrance on a first side (e.g., the entrance side 112), and tunnel exit on a second side (e.g., the exit side 114). In some instances, the tunnel 202 may be composed of a high-density polyethylene. In other instances, the tunnel 202 may be composed of plastic, wood, metal, or similar rigid materials. The tunnel 202 may be composed of a material that blocks or is resistant to the sanitizing agent 118 and/or UV light. In various embodiments, the sensor 122 may be coupled to the tunnel 202 for detecting the object 110. The tunnel 202 may be coupled to some, all, or none of the structures of the sanitization system 100. For instance, some or all of the structures may provide support for the tunnel 202, or the tunnel 202 may be freestanding and may not require support from any of the structures of the sanitization system 100.

Figure 3:
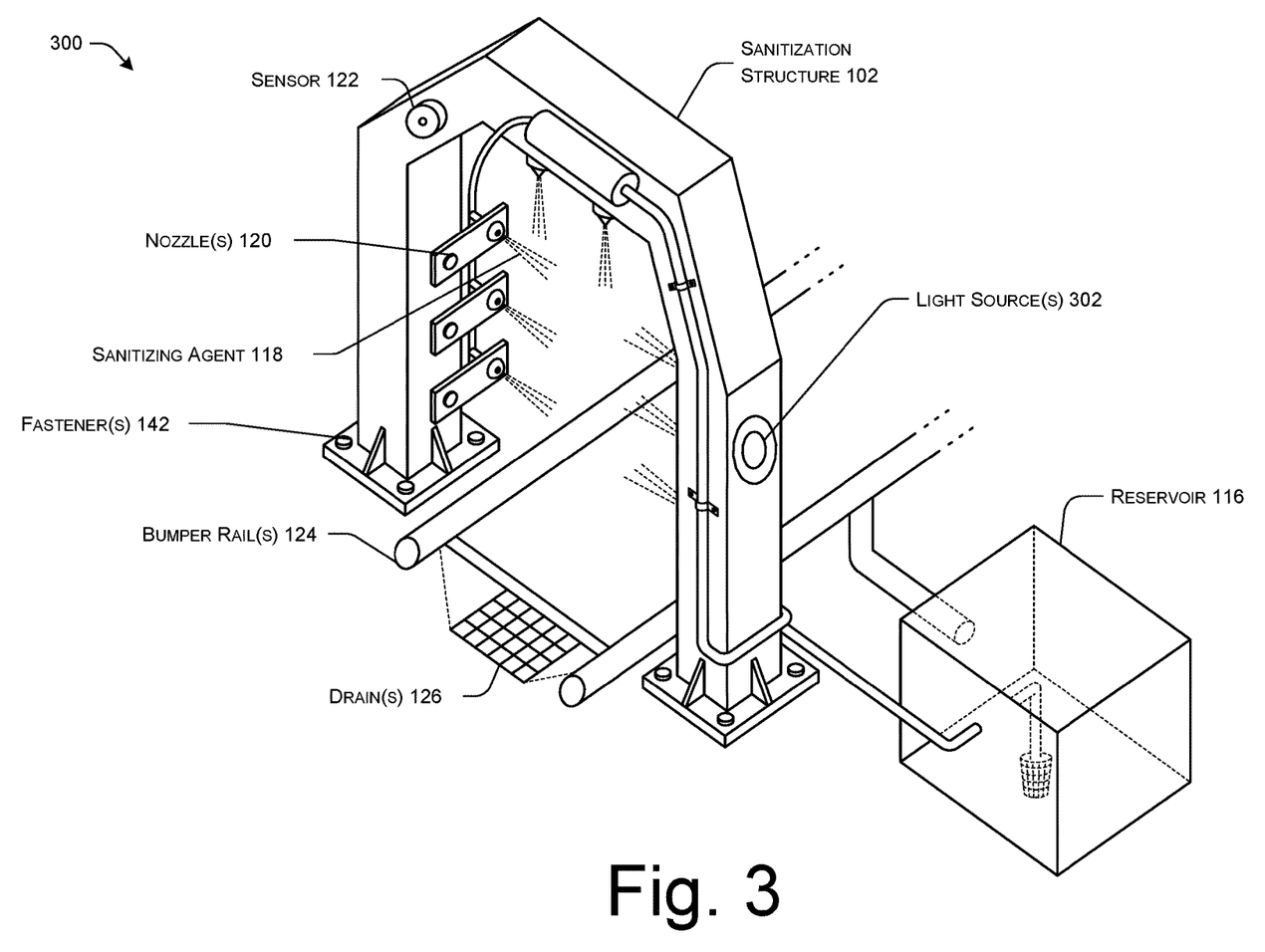
FIG. 3 is a pictorial diagram of an illustrative system that includes a sanitization structure to facilitate application of a sanitizing agent to one or more objects.

FIG. 3 is a pictorial diagram 300 of an illustrative system that includes a sanitization structure 102 to facilitate application of a sanitizing agent 118 to one or more objects 110. As shown, the sanitization structure 102 may be coupled to a reservoir 116 and one or more nozzles 120. As shown, the one or more nozzles 120 appear to be coupled to an inside side of the sanitization structure 102. The one or more nozzles 120 may be arranged on the inside side of the sanitization structure 102 to apply the sanitizing agent 118 to the entirety (e.g., each side) of an object 110. For instance, and as shown, the sanitization structure 102 appears to be depicted as having three nozzles 120 on a first inside side of an arch, two nozzles 120 on a second inside side of the arch (e.g., the top side), and three nozzles 120 on a third inside side of the arch. A position of the one or more nozzles 120 may be based on a size or a shape of the object(s) 110. In some instances, the one or more nozzles 120 may be moveable and may be coupled to the sanitization structure 102 on a track or groove such that the one or more nozzles 120 may be placed at various positions along the inside side of sanitization structure 102. The one or more nozzles 120 may also be rotatable. For instance, the one or more nozzles 120 may rotate and/or adjust while maintaining a first position along an inside surface of the sanitizations structure 102. In alternative embodiments, the sanitization structure 102 may also be configured to have one or more additional nozzles 120 that are located underneath an object 110. For instance, the sanitization structure 102 may be a loop and/or a ring with one or more additional nozzles 120 that are aimed at an underside of an object 110.

As shown, the one or more nozzles 120 appear to apply a sanitizing agent 118. The sanitizing agent 118 may be an anti-microbial solution that is composed of a chemical that removes, disables, and/or destroys pathogens. For instance, a pathogen may be a pathogenic organism that includes at least one of viruses, bacteria, fungi, protozoa, or parasites. A pathogen may be referred to as a germ. Application of the sanitizing agent 118 may also remove food products, bodily fluids, dirt, or any other substance from the object(s) 110. In various embodiments, the sanitizing agent 118 may be selected for application to the object 110 based on desired removal of a particular pathogen or pathogens. In some instances, the one or more nozzles 120 may apply a mist and/or liquid to an object 110.

As shown, the reservoir 116 appears to be coupled to the one or more nozzles 120 via a tube and/or pipe that carries a liquid (e.g., water) and/or a sanitizing agent 118 (e.g., a chemical that may or may not be combined with water). The sanitizing agent 118 may be pumped to the one or more nozzles 120 by a pressurized system that includes at least a zone control valve (or any other type of valve). As shown, a sensor 122 (e.g., a motion sensor) may detect an object 110. In response to detecting the object 110, the pressurized system may open the zone control valve allowed the sanitizing agent 118 to be applied to the object 110 via the one or more nozzles 120. As shown the sanitization structure 102 may be permanently or removably fastened to the ground (e.g., concrete) or to a surface (e.g., a platform) via fasteners 142. As shown, bumper rails 124 appear to be depicted in an opening in the sanitization structure 102 in order to guide an object 110 underneath, along an inside side, of the sanitization structure 102. As shown, a light source 302 (e.g., an indicator light) may indicate that the sanitizing agent 118 is currently being applied to the object 110 and/or the one or more nozzles 120 are currently emitting the sanitizing agent 118. In other instances, the light source 302 may turn on (e.g., emit a colored light such as a green light) in response to detecting the object 110 by the sensor 122. In some instances, the light source 302 may emit a second colored light (e.g., a yellow light) to indicate at least one of the sanitization structure 102, the drying structure 104, the UV light structure 106, and/or the UV curtain structure 108 warming-up and/or preparing for operation. The light source 302 may emit a third colored light (e.g., a red light) to indicate a failure (e.g., a mechanical and/or electrical failure) in the system. The red light may also indicate a maintenance need of one or more of the structures. For instance, the red light may indicate that an air purifier 130 coupled the drying arch 104 needs to be replaced due to it being defective.

As show, a drain 126 appears to be depicted underneath, or proximal, to the sanitization structure 102. Although any number of drains 126 are contemplated herein, the drain 126 may be configured to capture liquid run-off, or sanitization agent 118 run-off, after and/or during application to the object 110 by the one or more nozzles 120. In some instances, the drain 126 may be coupled to the reservoir 116 to recycle and/or reuse the sanitizing agent 118 for application to subsequent objects 110. In some instances, the drain 126 may include a funnel and/or a grated floor. In some instances, the drain 126 may include a basin or collection tank that is configured to store excess sanitizing agent 118, or sanitizing agent 118 that has yet to be applied to the object(s) 110.

Figure 4A:
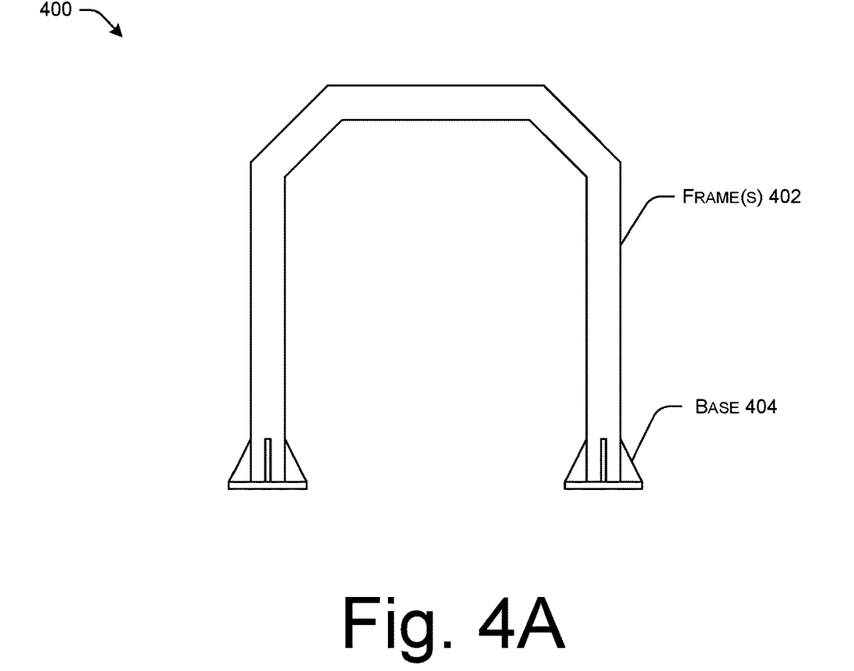
FIG. 4A is a pictorial diagram of an illustrative system that includes a frame and a base of a structure that facilitates sanitization of one or more objects.

FIG. 4A is a pictorial diagram 400 of an illustrative structure of the sanitization system 100 that includes a frame and a base of the structure. The sanitization structure 102, drying structure 104, the UV light structure 106, and the UV curtain structure 108 may include a frame 402. The frame 402 may be a structural frame that incorporates at least columns, arches, and/or beams to bear weight and/or carry a load. For instance, the frame 402, with respect to the sanitization structure 102, may be configured to couple to, and carry the weight of, the one or more nozzles 120. The frame 402, may include horizontal beams, vertical beams, non-horizontal and non-vertical beams, and/or rounded beams. The frame 402 may be an arch. In some instances, the frame 402 may be a rectangular three-dimensional shape. The frame 402 may be made of a material, or multiple materials. For instance, the frame may be composed of a rigid material including metal (e.g., aluminum), wood, and/or plastic. The frame 402 may also include a base 404. The base may be configured to allow the frame 402 to be permanently or removably coupled to the ground (e.g., concrete) or a surface (e.g., a platform) via one or more fasteners 142. For instance, the base 404 may have one or more holes or openings that allow a fastener 142 to pass through to the ground/surface.

Figure 4B:
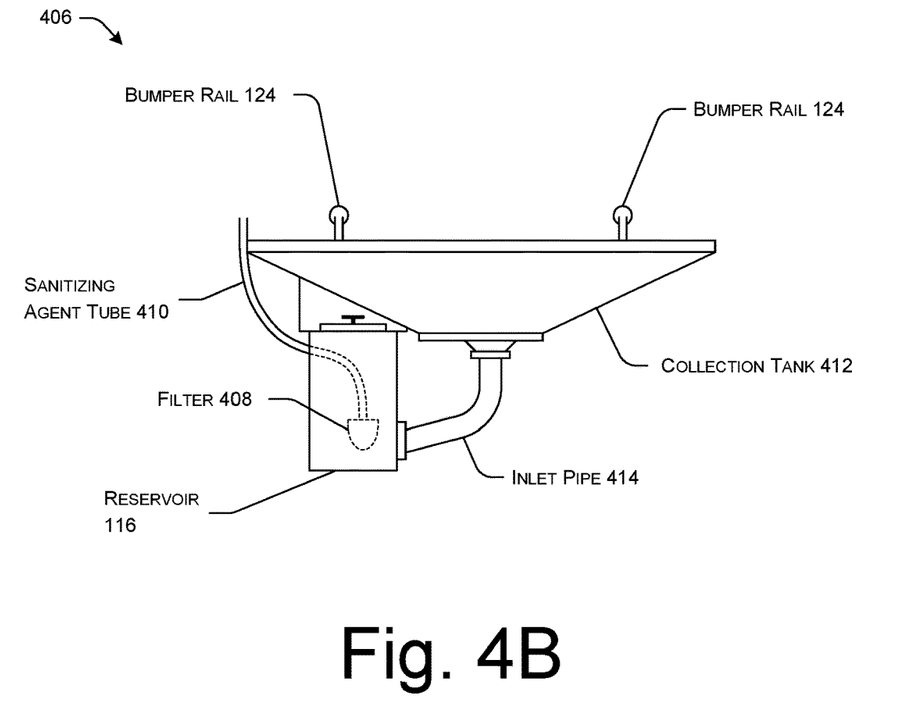
FIG. 4B is a pictorial diagram of an illustrative system that includes at least a reservoir, a filter, and a sanitizing agent tube with respect to a sanitization structure.

FIG. 4B is a pictorial diagram 406 of an illustrative apparatus that includes a reservoir 116, a filter 408, and a sanitizing agent tube 410 with respect to the sanitization structure 102. In various embodiments, the reservoir 116 may contain a solution comprised of liquid (e.g., water) and/or the sanitizing agent 118. The solution may pass through the filter 408 to remove contaminants, such as dirt. In some instances, the solution may be pumped via a pressurized system via a sanitizing agent tube 410 to the one or more nozzles 120 for application to an object 110 (e.g., a shopping cart). As shown, a collection tank 412 may be coupled to the drain 126 and/or configured to collect run-off of the sanitizing agent 118 that was applied by the one or more nozzles 120 to the object(s) 110. As shown, the collection tank appears be coupled to an inlet tube 414. The inlet tube 414 may carry, deliver, or transport the sanitizing agent 118 collected in the collection tank 412 to the reservoir 116.

Figure 5:
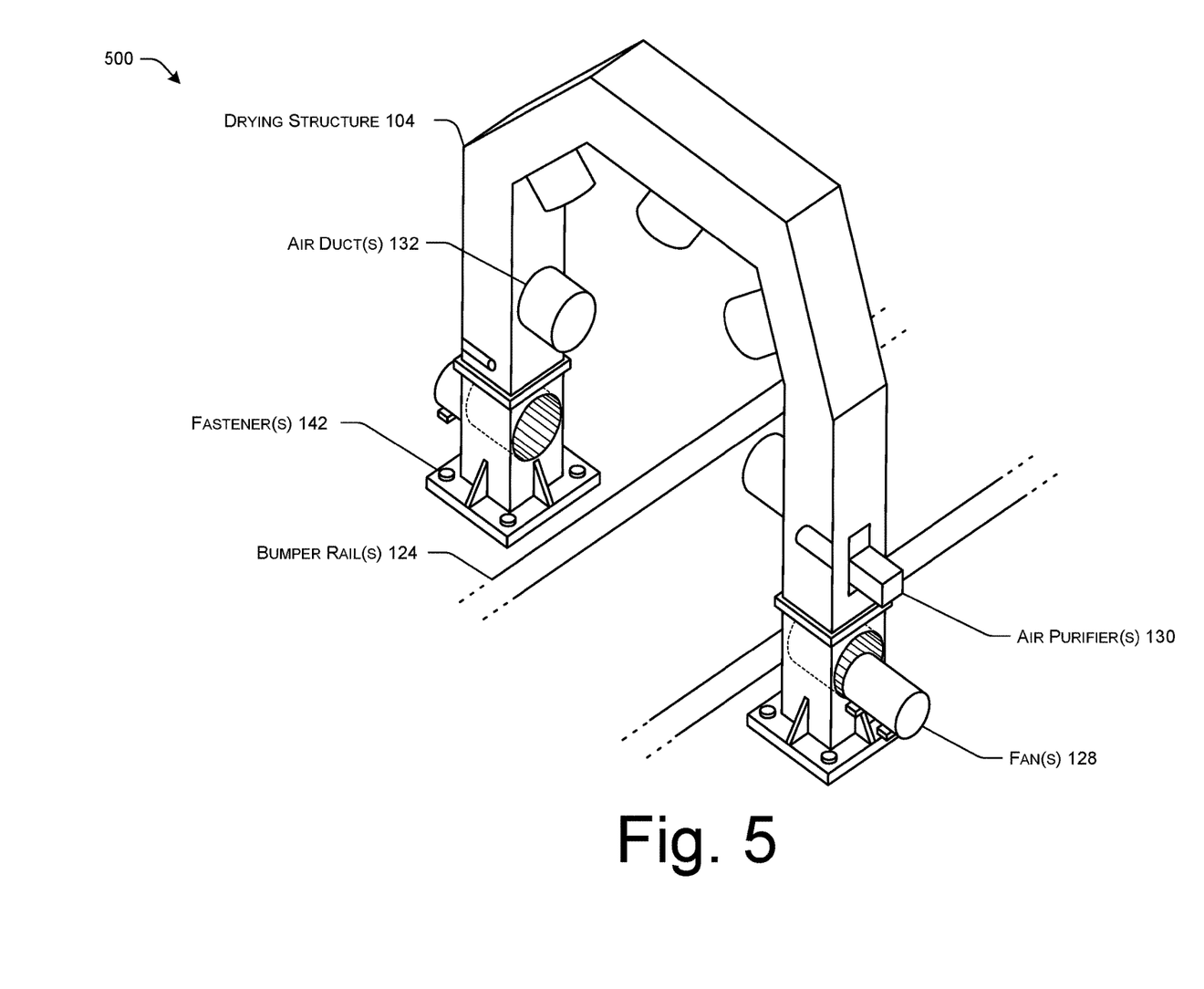
FIG. 5 is a pictorial diagram of an illustrative system that includes a drying structure to facilitate application of a gas current to one or more objects.

FIG. 5 is a pictorial diagram 500 of an illustrative apparatus that includes a drying structure 104 to facilitate application of a gas current to one or more objects 110. As shown, the drying structure 104 appears to be coupled to one or more fans 128. The one or more fans 128 may be a high-pressure blower with a minimum and maximum revolutions per minute (RPM). The one or more fans 128 may be enclosed in cages for protection purposes. In some instances, the one or more fans 128 may collect or draw gas (e.g., air) from the atmosphere. The one or more fans 128 may include one or more RPM settings (e.g., a maximum setting of 3600 RPM). The one or more fans 128 may provide a gas to the one or more air purifiers 130 or air scrubbers for purification. The one or more air purifiers 130 may convert unpurified gas (e.g., air) into purified gas (e.g., air with contaminants and/or dust particles removed). The one or more air purifiers 130 may utilize UV ozone purification. For instance, unpurified air may be infused with colony fighting organisms that disable airborne bacterial organisms. The one or more air purifiers 130 and the one or more fans 128 may provide a gas current (e.g., purified air), to the one or more air ducts 132. As shown, the drying structure 104 may be coupled to one or more air ducts 132 that apply a gas current to the object(s) 110 (e.g., the shopping cart). As shown, the one or more air ducts 132 appear to be arranged along an inside side of the drying structure 104.

As shown, the drying structure 104 appears to be coupled to five air ducts 132. A position of the one or more air ducts 132 may be based on a size or a shape of the object(s) 110.

In some instances, the one or more air ducts 132 may be coupled to the drying structure 104 on a track or groove such that the one or more air ducts 132 may be moved and placed at various positions on the drying structure 104.

At least one air duct 132 of the one or more air ducts 132 may be configured to have an adjustable opening (e.g., an adjustable diameter and/or cross-sectional area). For instance, an opening of the at least one air duct 132 may have a default opening configuration to apply a gas current at a first speed. The default opening configuration may include an opening (i.e., to apply a gas current to the object 110) that is a first cross-sectional area. The opening of the at least one air duct 132 may be adjusted to have a high-speed opening configuration with a second cross-sectional area that is smaller than the first cross-sectional area. In various embodiments, a plurality of air ducts 132 may be arranged to create an air curtain. For instance, a first air duct 132 may be configured to apply a first gas current at a first angle, a second air 132 duct may be configured to apply a second gas current at a second angle, and a third air duct 132 may be configured to apply a third gas current at a third angle such that the first gas current, the second gas current, and the third gas current at last partially intersect, thereby allowing the gas current to make contact with each surface of the object(s) 110. In alternative embodiments, the drying structure 104 may also be configured to have one or more additional air ducts 132 that are located underneath an object 110. For instance, the drying structure 104 may be a loop and/or a ring with one or more additional air ducts 132 that may be aimed at the underside of an object 110. The drying structure 104 may be permanently or removably fastened to the ground (e.g., concrete) or a surface (e.g., a platform) via one or more fasteners 142. As shown, bumper rails 124 appear to be configured to provide a guide for an object(s) 110 to pass through and/or underneath the drying structure 104.

In various embodiments, one or more fans 128, the one or more air purifiers 130, and the one or more air ducts 132 may be connected and/or coupled together via a purification tunnel. A purification tunnel may be a pipe and/or tube that facilitates the movement of a gas (e.g., air) between the one or more fans 128, the one or more air purifiers 130, and the one or more air ducts 132.

Figure 6:
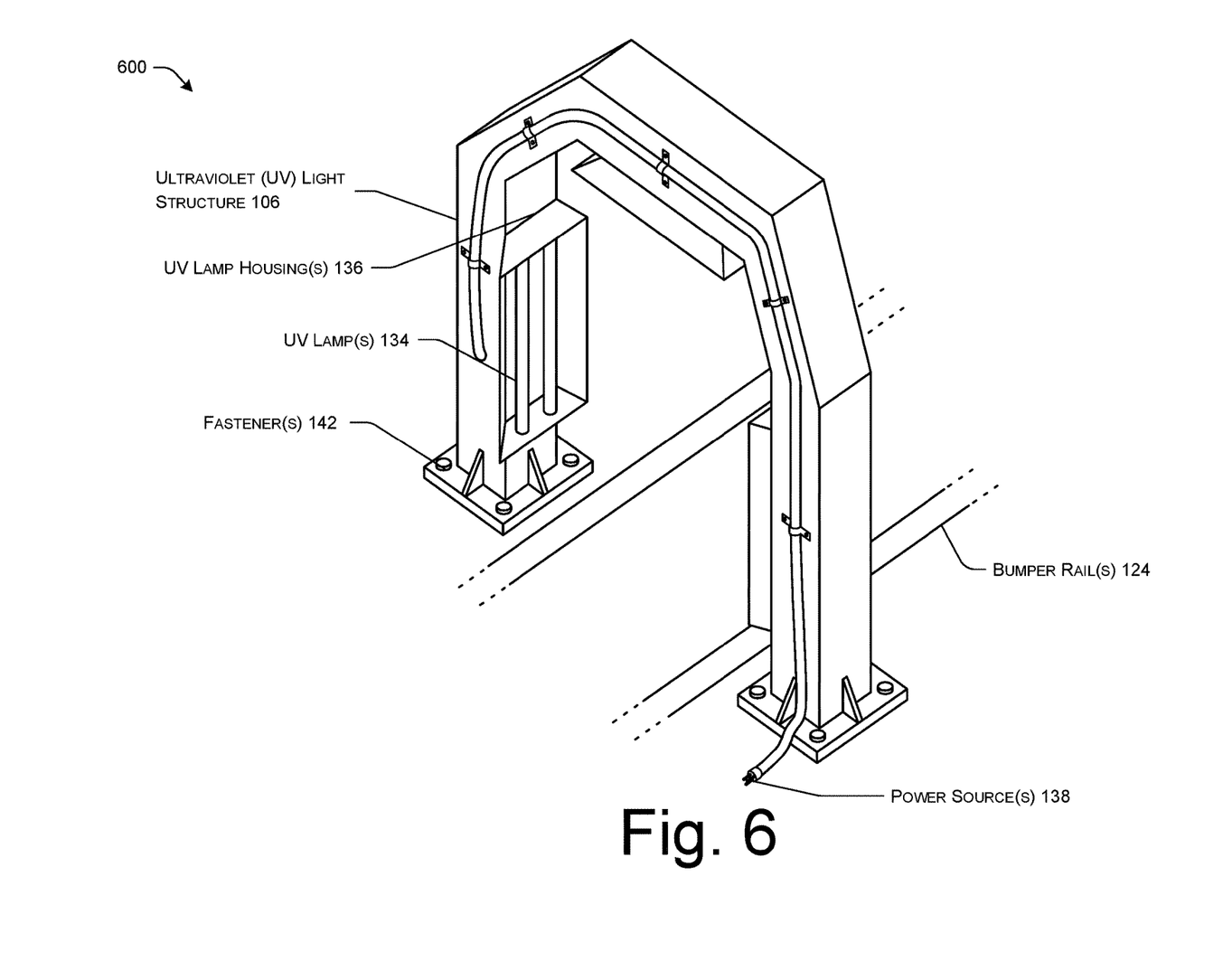
FIG. 6 is a pictorial diagram of an illustrative system that includes an ultraviolet (UV) light structure to facilitate application of UV light to one or more objects.

FIG. 6 is a pictorial diagram 600 of an illustrative system that includes an ultraviolet (UV) light structure 106 to facilitate application of UV light to one or more objects 110. As shown, the UV light structure 106 appears to be coupled to one or more UV lamps 134. The one or more UV lamps 134 may be housed in one or more UV lamp housings 136. The one or more UV lamp housings 136 may provide a coupling mechanism to configure the one or more UV lamps 134 to be coupled to the UV light structure 106. In addition, the one or more UV lamp housings 136 may block at least a portion of the UV light emitted from the one or more UV lamps 134. The one or more UV lamps 134 may be one or more germicidal UV lamps 134 that disable and/or destroy pathogens (e.g., bacteria, fungi, protozoa, viruses, and/or parasites). A first UV lamp 134 of the one or more UV lamps 134 may include a first UV setting (e.g., UV-C with a wavelength from 100 nm to 280 nm), a second UV lamp 134 may include a second UV setting (e.g., UV-B with a wavelength from 280 nm to 315 nm), and/or a third UV lamp 134 may include a third UV setting (e.g., UV-A with wavelength from 315 nm to 400 nm). The UV light structure 106 may be permanently or removably fastened to the ground (e.g., concrete) or a surface (e.g., a platform) via one or more fasteners 142. In various embodiments, the one or more UV lamps 134 may emit UV light that has a wavelength between ten and 400 nanometers. The application of UV light to an object 110 may disable and/or destroy pathogens (e.g., bacteria). For instance, UV light may be electromagnetic radiation that is mutagenic (i.e., alters the genetic material or deoxyribonucleic acid (DNA) of bacteria). In some instances, the UV light may break the molecular bonds of microorganismal DNA. As shown, bumper rails 124 appear to be configured to provide a guide for the object(s) 110 to pass through and/or underneath the UV light structure 106.

Figure 7:
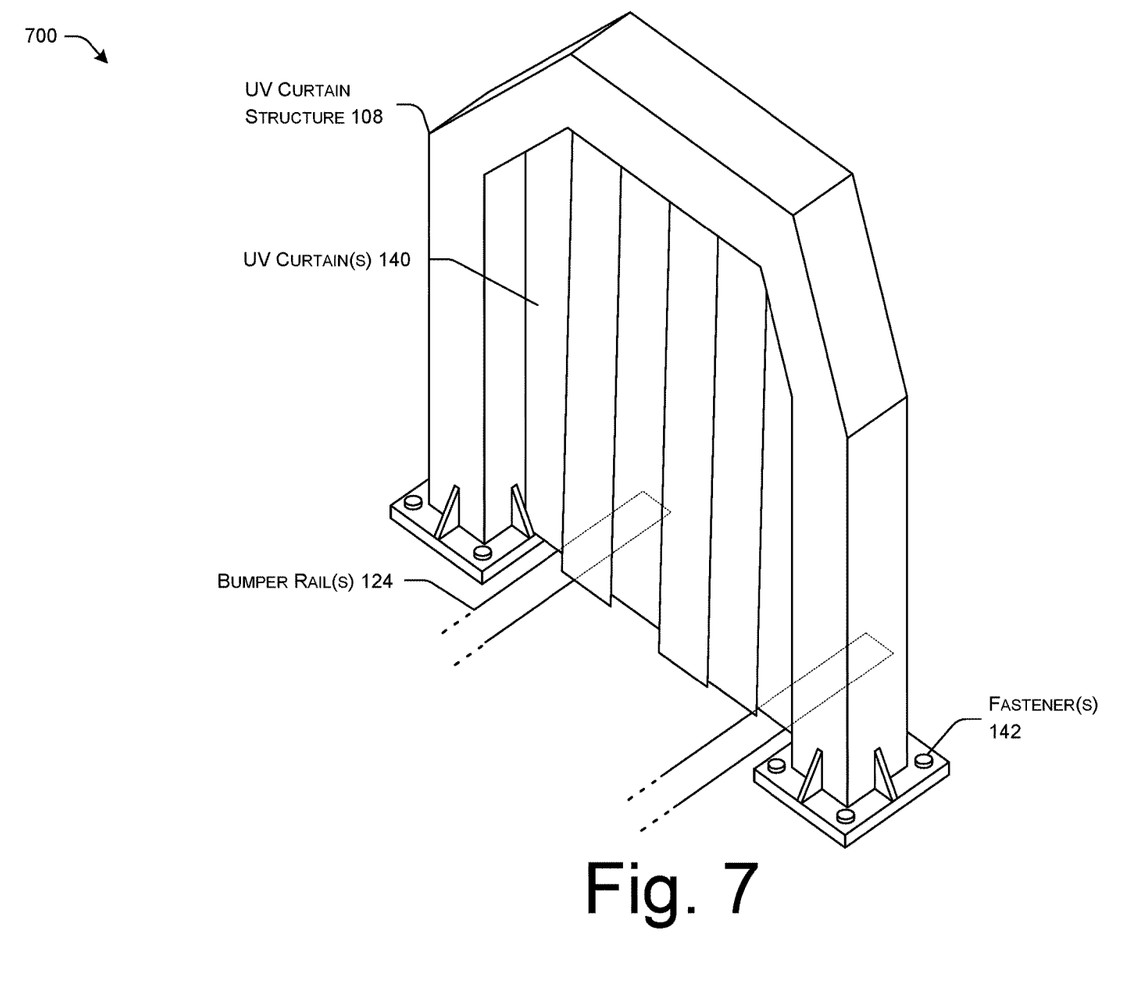
FIG. 7 is a pictorial diagram of an illustrative system that includes a UV curtain structure to facilitate blocking UV light applied by a UV light structure.

FIG. 7 is a pictorial diagram 700 of an illustrative apparatus that includes a UV curtain structure 108 to facilitate blocking UV light. As shown, the one or more UV curtain 140 may be composed of a material that blocks UV light. For instance, the one or more UV curtains 140 may be composed of an amber-tinted poly-vinyl chloride material that is able to block at a least a portion of the UV light emitted from the one or more UV lamps 134. As shown, the one or more UV curtains 140 appear to be depicted as a curtain with slits that allow an object 110 to pass through. Alternatively, the one or more UV curtains 140 may be a single curtain. The UV curtain structure 108 may be permanently or removably fastened to the ground (e.g., concrete) or a surface (e.g., a platform) via one or more fasteners 142. As shown, bumper rails 124 appear to be configured to provide a guide for the object(s) 110 to pass through and/or underneath the UV curtain structure 108.

Figure 8:
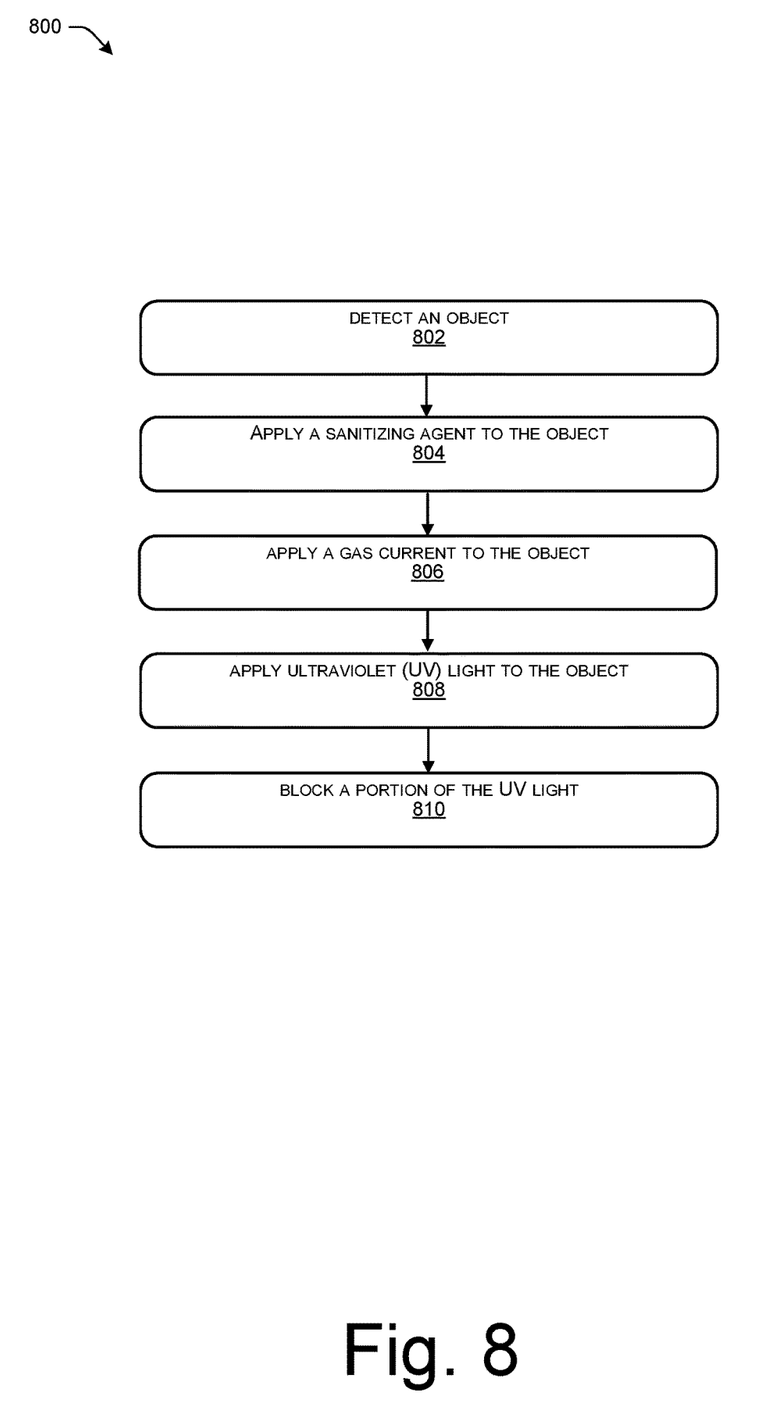
FIG. 8 is a flow diagram illustrating an example process for sanitizing one or more objects.

FIG. 8 is a flow diagram 800 illustrating an example process for sanitizing an object. For the purposes of this discussion, the operations illustrated in FIG. 8 may be performed by at least the sanitization structure 102, the drying structure 104, the UV light structure 106, and/or the UV curtain structure 108.

Block 802 illustrates detecting an object (e.g., a shopping cart, a hospital bed, a wheelchair, etc.). For instance, one or more sensors 122 (e.g., a motion sensor), may detect the object 110 at an entrance side 112 of at least one of the sanitization structure 102, the drying structure 104, the UV light structure 106, or the UV curtain structure 108. In some instances, the object(s) 110 may be configured to transmit a signal that may be received by the sensor(s) 122.

Block 804 illustrates applying a sanitizing agent to the object. The sanitizing agent 118 may be applied to the object(s) 110 via one or more nozzles 120 coupled to the sanitizing structure 102. In various embodiments, the sanitizing agent 118 may apply a mist to the object(s) 110. In some instances, the sanitizing agent 118 may be applied to the object(s) 110 in response to detecting the object(s) 110 via the sensor(s) 122. The one or more nozzles 120 may be configured to apply a continuous stream to the object(s) 110. A configuration of the one or more nozzles 120 may be based on a size or shape of the object(s) 110. The sanitizing agent 118 may be a chemical that is configured to remove, destroy, and/or disable various pathogens (or any other substance, such as food products, bodily fluids, dirt, etc.).

Block 806 illustrates applying a gas current to the object. A gas current (e.g., purified air) may be applied to the object(s) 110 via one or more air ducts 132 coupled to the drying structure 104. In various embodiments, the gas current may be obtained by drawing in air from the atmosphere via one or more fans 128 coupled to the drying structure 104 and purifying the air via one or more air purifiers 130 coupled to the drying structure 104. A configuration of the one or more air ducts 132 may be based on a size or shape of the object(s) 110. The one or more air ducts 132, the one or more air purifiers 130, and the one or more fans 128 may be connected via a pipe and/or tube.

Block 808 illustrates applying UV light to the object. UV light may be applied to the object(s) 110 via one or more UV lamps 134. The one or more UV lamps 134 may emit germicidal UV light that disables or destroys one or more pathogens. In various embodiments, the one or more UV lamps 134 may be coupled to the UV light structure 106 directly or indirectly via one or more UV lamp housings 136.

Block 810 illustrates blocking at least a portion of the UV light emitted by one or more UV lamps. In various embodiments, one or more UV light curtains 140 may be composed of a material that is able to block at least a portion of the UV light emitted by the one or more UV lamps 134. That way, potentially harmful UV light that is emitted by the UV lamp(s) 134 may not be exposed to individuals in proximity to the sanitization system 100, or the UV curtain(s) 140 may at least minimize the amount of UV light that escapes the sanitization system 100.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. An apparatus comprising:
   a structure that includes one or more components that prevent at least a portion of light from exiting the apparatus;
   a light component that is associated with the structure and that is configured to apply the light to an object within the structure;
   a drying component that is configured to apply a gas current to the object, the gas current including a purified gas, wherein the drying component is moveable or configurable based at least in part on a size or a shape of the object;
   a fan that is coupled to the drying component and that is configured to receive unpurified gas;
   a purification tunnel that is configured to convert the unpurified gas into the purified gas; and
   an opening in which the object at least one of:
   enters the structure; or
   exits the structure.

2. The apparatus as recited in claim 1, further comprising a sanitization component that includes one or more nozzles that are configured to apply a sanitizing agent to the object.

3. The apparatus as recited in claim 1, wherein the opening is a first opening in which the object is placed within the structure, and further comprising a second opening in which the object is removed from the structure.

4. The apparatus as recited in claim 1, wherein the light component includes one or more ultraviolet (UV) lamps and the light is UV light.

5. The apparatus as recited in claim 1, further comprising a component that is configured to allow a user to discontinue applying the light to the object.

6. An apparatus comprising:
   an entrance in which an object enters the apparatus;
   a light component that is configured to apply light to the object;
   a drying component that is configured to apply a gas current to the object, the gas current including a purified gas, wherein the drying component is moveable or configurable based at least in part on a size or a shape of the object;
   a fan that is coupled to the drying component and that is configured to receive unpurified gas;
   a purification tunnel that is configured to convert the unpurified gas into the purified gas;
   an exit, different than the entrance, through which the object exits the apparatus; and
   one or more components that are configured to block at least a portion of the light from escaping the apparatus via the entrance or the exit.

7. The apparatus as recited in claim 6, further comprising a sensor that is configured to detect the object, and in response to detecting the object, cause the light to be applied to the object.

8. The apparatus as recited in claim 7, further comprising a component, different than the one or more components, that is configured to allow a user to discontinue applying the light to the object.

9. The apparatus as recited in claim 6, further comprising:
   a sanitization component that includes one or more nozzles that are configured to apply a sanitizing agent to the object; and
   a reservoir that is coupled to the sanitization component and that stores the sanitizing agent.

10. The apparatus as recited in claim 9, wherein:
    the sanitization component applies the sanitizing agent to the object at a first time;
    the drying component applies the gas current to the object at a second time that is subsequent to the first time; and
    the light component applies the light to the object at a third time that is subsequent to the second time.

11. The apparatus as recited in claim 9, wherein:
    the sanitizing agent is evaporable; or
    the purified gas is applied to the object to evaporate the sanitizing agent and to dry the object.

12. The apparatus as recited in claim 6, further comprising a conveyor that transports the object from the entrance, through the apparatus, and out of the exit.

13. The apparatus as recited in claim 6, wherein the light component includes one or more UV lamps and the light is UV light.

14. The apparatus as recited in claim 6, further comprising a power source coupled to the apparatus.

15. The apparatus as recited in claim 6, wherein the object is pushed into the entrance by a conveyor or a user and is pulled out of the exit by the conveyor or the user.

16. The apparatus as recited in claim 6, wherein the purification tunnel is a tube or pipe through which the unpurified gas or the purified gas moves.

17. The apparatus as recited in claim 6, wherein the purification tunnel is an air scrubber that removes one or more gases or particles from the unpurified gas to generate the purified gas.

18. An apparatus for sanitizing an object comprising:
    a sanitization component that includes one or more nozzles that are configured to apply a sanitizing agent to the object;
    a drying component that includes one or more air ducts that are configured to apply a gas current to the object, the gas current including a purified gas;
    a fan that is coupled to the drying component and that is configured to receive unpurified gas;
    a purification tunnel that is coupled to the fan and an air duct of the one or more air ducts, and that is configured to convert the unpurified gas into the purified gas;
    a light component that includes one or more lamps that are configured to apply UV light to the object, wherein the one or more nozzles and the one or more air ducts are moveable and configurable based at least in part on a size and a shape of the object;
a UV curtain component that is configured to block a portion of the UV light; and
an entrance side at which the object enters the apparatus and an exit side at which the object exits the apparatus.

19. The apparatus as recited in claim 18, further comprising a motion sensor that is coupled and communicatively coupled to at least one of the sanitization component, the drying component, or the light component, the motion sensor configured to:
   detect the object;
   in response to detecting the object, at least one of cause the sanitization component to apply the sanitizing agent to the object via the one or more nozzles, cause the drying component to apply the gas current to the object, or cause the light component to apply the UV light to the object;
   determine that the object is no longer detected; and
   based at least in part on determining that the object is no longer detected, at least one of cause the sanitization component to cease applying the sanitizing agent, cause the drying component to cease applying the gas current, or cause the light component to cease applying the UV light.

20. The apparatus as recited in claim 18, further comprising:
   a first bumper rail that extends from a first side of the sanitization component to a first side of the UV curtain component;
   a second bumper rail that is substantially parallel to the first bumper rail and that extends from a second side of the sanitization component to a second side of the UV curtain component; and
   a drain that is between the first bumper rail and the second bumper rail.

* * * * *